United States Patent
Cumbie et al.

(10) Patent No.: US 11,326,200 B2
(45) Date of Patent: May 10, 2022

(54) METHOD OF PREPARING TEST SAMPLES

(71) Applicant: HEWLETT-PACKARD DEVELOPMENT COMPANY, L.P., Houston, TX (US)

(72) Inventors: Michael W. Cumbie, Corvallis, OR (US); Devin Alexander Mourey, Corvallis, OR (US); Si-Iam Choy, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 369 days.

(21) Appl. No.: 16/094,360

(22) PCT Filed: Jul. 22, 2016

(86) PCT No.: PCT/US2016/043667
§ 371 (c)(1),
(2) Date: Oct. 17, 2018

(87) PCT Pub. No.: WO2018/017131
PCT Pub. Date: Jan. 25, 2018

(65) Prior Publication Data
US 2019/0119723 A1   Apr. 25, 2019

(51) Int. Cl.
| | |
|---|---|
| C12Q 1/6806 | (2018.01) |
| B01L 3/02 | (2006.01) |
| B01L 3/00 | (2006.01) |
| G01N 1/28 | (2006.01) |
| C12Q 1/68 | (2018.01) |
| B01J 19/00 | (2006.01) |
| C12Q 1/686 | (2018.01) |

(52) U.S. Cl.
CPC ........ *C12Q 1/6806* (2013.01); *B01J 19/0046* (2013.01); *B01L 3/0268* (2013.01); *B01L 3/5088* (2013.01); *B01L 3/50853* (2013.01); *C12Q 1/68* (2013.01); *C12Q 1/686* (2013.01); *G01N 1/28* (2013.01); *G01N 1/2806* (2013.01); *B01J 2219/0065* (2013.01); *B01J 2219/00378* (2013.01); *B01J 2219/00385* (2013.01); *B01J 2219/00527* (2013.01); *B01J 2219/00599* (2013.01); *B01J 2219/00659* (2013.01); *B01J 2219/00722* (2013.01); *B01L 2200/0673* (2013.01); *G01N 2001/282* (2013.01)

(58) Field of Classification Search
CPC .................................................. C12Q 1/6806
See application file for complete search history.

(56) References Cited

U.S. PATENT DOCUMENTS

| | | | |
|---|---|---|---|
| 6,221,653 B1 | 4/2001 | Caren et al. | |
| 6,458,583 B1 | 10/2002 | Bruhn et al. | |
| 6,664,044 B1 | 12/2003 | Sato | |
| 8,658,430 B2 | 2/2014 | Miller et al. | |
| 2006/0046266 A1 | 3/2006 | Kuk et al. | |
| 2011/0159547 A1 | 6/2011 | Yu et al. | |
| 2012/0220497 A1* | 8/2012 | Jacobson | B82Y 30/00 506/16 |
| 2014/0363821 A1 | 12/2014 | Bashir et al. | |

FOREIGN PATENT DOCUMENTS

| | | |
|---|---|---|
| CN | 103028354 A | 4/2013 |
| RU | 2385940 | 4/2010 |

OTHER PUBLICATIONS

Temiz, Lab-on-a-chip devices: How to close and plug the lab? Microelectronic Engineering, 132: 156-175, 2015. (Year: 2015).*

Hanyoup Kim et al: "Petri Dish PCR: Laser-Heated Reactions in Nanoliter Droplet Arrays"; Lab on a Chip; vol. 9, No. 9; Jan. 1, 2009; p. 1231, col. 2, Lines 14-22; Figure 1a.

Yingnan Sun et al; "A Novel Picoliter Droplet Array for Parallel Real-Time Polymerase Chain Reaction Based on a Double-Inkjet Printing"; Lab on a Chip; vol. 14, No. 18; Jan. 1, 2014; pp. 3603-3610.

Madou; "Ink-Jet"; Feb. 12, 2011; http://dionisio.centropiaggio.unipi.it/gvozzi/Shared%20Documents/Micro%20e%20Nano%20Sistemi/Tecnologie%203D/Inkjet/inkjet_madou.pdf.

Mueller; "Quantitative Analysis of PCR Fragments with the Agilent 2100 Bioanalyzer"; Jul. 27, 2000; http://www.chem-agilent.com/pdf/5968-7496EN.pdf.

* cited by examiner

*Primary Examiner* — Samuel C Woolwine
*Assistant Examiner* — Carolyn L Greene
(74) *Attorney, Agent, or Firm* — Fabian VanCott (57) ABSTRACT

A method of preparing a sample may include depositing an aqueous solution comprising copies of a primer into a layer of hydrophobic liquid on a substrate with a thermal inkjet device. A sample may include: a substrate; a layer of hydrophobic liquid on the substrate, the layer of hydrophobic liquid comprising a plurality of droplets of aqueous solution distributed in the layer, wherein the plurality of droplets contain: primers; a polymerase enzyme; deoxynucleotide triphosphates (dNTPs); and a target sequence for replication; and a cover, the cover contacting and covering the layer of hydrophobic liquid.

17 Claims, 6 Drawing Sheets

420
Depositing an aqueous solution comprising copies of a primer into a layer of hydrophobic liquid on a substrate with a thermal inkjet device.

METHOD OF PREPARING TEST SAMPLES

BACKGROUND

Genetic testing has seen rapid and increasingly practical applications being developed for the identification of specific gene variants in samples. Identification of the BRCA mutations is perhaps the most common genetic test in current clinical practice. However, the human genome is estimated to contain approximately 25,000 genes. Even when every gene is identified and all the alleles are documented, providing testing for an individual may continue to consume non-trivial amounts of resources.

BRIEF DESCRIPTION OF THE DRAWINGS

The accompanying drawings illustrate various examples of the principles described herein and are a part of the specification. The illustrated examples do not limit the scope of the claims. Throughout the drawings, identical reference numbers designate similar, but not necessarily identical, elements.

DETAILED DESCRIPTION

Polymerase chain reaction (PCR) is one of the defining technologies of genetics, PCR is a method of replicating a single strand of genetic material to produce a large enough sample to test, PCR uses a series of operations that are repeated, with each cycle approximately doubling the number of copies of the test sequence. PCR may be performed by placing a test sample in a solution. The solution also contains master mix. Master mix contains the enzymes and protein precursors to permit replication. The solution also contains primers. In some examples, the primers are of a single type. In other examples, a variety of primers are included.

The solution is then subjected to thermal cycling. With each cycle, the target sequence and any copies of the target sequence perform the following actions: 1) bind a primer, 2) form a complimentary sequence to the target, and 3) melt and dissociate the new and old sequences. With each cycle the number of copies of the target doubles.

A wide variety of specific approaches and variant methodologies exist that use this basic framework. One of these approaches is digital PCR (dPCR). Genetic material amplified by PCR was traditionally subjected to a separation technique such as southern blot or western blot in order to generate a peak or peaks for fragment weight. This produced a qualitative output. Specifically, a peak was either present or not present. Certain peak patterns after an enzymatic cutting process indicated the locations of certain sequences in the target corresponding to the cutting enzyme used.

Traditional PCR amplifies a target in a single solution. In contrast, dPCR separates the solution in to a large number of small samples, often in individual wells or similar, and then amplifies each of the small samples. Thus, each of the starting samples either contains or does not contain a copy of the target. In samples where the target is present, amplification occurs. In samples where no target is present, no amplification occurs. Often, the solution volume is selected to limit the volume to a single copy of the target. This provides a uniformity of sample intensity over the samples. Thus, each sample provides a binary output of present or not present. However, when thousands of samples are combined, the sum of the outputs produces a count out of a given number of samples or a percentage. Accordingly, dPCR is a pseudoquantitative methodology.

Many variant PCR techniques exist, including droplet digital PCR (ddPCR) and quantitative real-time PCR (qPCR). Droplet digital PCR is a version of dPCR which performs digital PCR in individualized droplets, as opposed to, for example, wells in a well plate. The droplets may be stored in a common vial or test solution. Quantitative real-time PCR (qPCR) monitors the progress of the PCR multiplication using a fluorescent dye or reporter. The dye or reporter allows detection of the quantity of double stranded DNA or specific sequences depending on the fluorescent source used. The ability to quantify the amount of DNA and the rate of DNA multiplication may be used to make determinations about the samples. Either of these techniques, as well as other PCR approaches, may be incorporated into the present disclosure as part of the described approaches.

In digital PCR, like most testing techniques, the greater number of samples, the smaller the expected error in a dPCR measurement. Examples described herein provide for a method to rapidly and cheaply produce a large number of dPCR samples for amplification and testing. Generally speaking, the time of dPCR testing may be divided into three areas: 1) forming the individual sample domains for amplification; 2) running the amplification; and 3) measuring the results. The example methods and devices described herein provide time savings in each of these portions of the test.

In one example, a large number of aqueous droplets in a hydrophobic liquid film are produced. The hydrophobic liquid may be mineral oil. In this example, the oil film reduces the evaporation rate of the droplets, allowing the size and concentration to stay relatively stable during the testing and evaluation. In one example, the deposition of the relatively large numbers of small liquid droplets is accomplished through the use of a modified inkjet printhead. In one example, this modified inkjet printhead is a thermal inkjet (TIJ) which uses a heating resistor to form an ejection bubble to propel a liquid droplet. In another example, this modified inkjet printhead is a piezoelectric inkjet (PIJ) which uses a piezoelectric actuator to eject the droplet. There has understandably been concern about the impact of the boiling temperatures produced by TIJ ejectors and the impact of that thermal spike on the viability of the enzymes in the master mix. In TIJ, however, the layer of fluid in contact with the heater element which reaches these extreme temperatures before drop ejection occurs is relatively small. In some estimates, less than 10 percent of the droplet volume is exposed to the higher temperatures. However, with some calibration, the impact may be accommodated and functional data produced. Because dPCR outputs a binary value for each sample domain, e.g. droplet, a slight reduction in amplification does not impact the accuracy or reliability of the methodology.

In one example, the droplets are ejected into a thin layer of hydrophobic liquid on a substrate. The substrate may be transparent and/or reflective. The cover is placed over the layer of hydrophobic liquid to protect the layer from disruption. In some examples, the cover includes a second layer of hydrophobic liquid on the side contacting the hydrophobic liquid. The result is a layer of hydrophobic liquid, for example, mineral oil, with a number of water based droplets suspended in the liquid layer. The layer is sandwiched between two sheets of material that support and protect the layer. This thin sandwich form may then be rapidly thermal cycled. The hydrophobic liquid facilitates thermal transfer to the droplets. The use of a thin and/or thermally conductive substrate and/or cover allows for a rapid change in temperature during amplification with minimal heat capacity to provide inertia. Finally, the droplets in the sheet may be measured. The droplets may be measured one at a time, for example, using a laser. The droplets may be measured in groups for example, using a scanner. The droplets may be measured en masse, for example, using an array of digital optical elements, such as a digital camera.

Forming the test domains as small droplets embedded in a hydrophobic liquid film allows reductions in time to 1) generate the domains, 2) cycle the domains to perform the amplification, and 3) measure the output of the domains. The final result also has the potential to be shelf stable. The small size of the aqueous droplets also reduces the impact of buoyancy with the droplets generally falling in the Stokes regime. Thus, test samples may be produced and measured but also retained at relatively low cost, allowing retesting or verification for a substantial length of time.

The present specification also describes a method of preparing a sample, the method including depositing an aqueous solution comprising copies of a primer into a layer of hydrophobic liquid on a substrate with a thermal inkjet device.

The present specification also describes a sample including: a substrate; a layer of hydrophobic liquid on the substrate, the layer of hydrophobic liquid including a plurality of droplets of aqueous solution distributed in the layer, wherein the plurality of droplets include primers; a polymerase; deoxynucleotide triphosphates (dNTPs); and a target sequence for replication; and a cover, the cover contacting and covering the layer of hydrophobic liquid.

The present specification also describes a system for preparing test samples, the system including: a printhead, the printhead containing an aqueous fluid comprising: water, primers, master mix, and a target sequence to be amplified; and a substrate positioned to receive a number of droplets ejected from the printhead, the substrate comprising: a layer of hydrophobic liquid on the substrate; wherein the number of droplets ejected by the printhead are embedded in the layer of hydrophobic liquid on the substrate.

Figure 1:
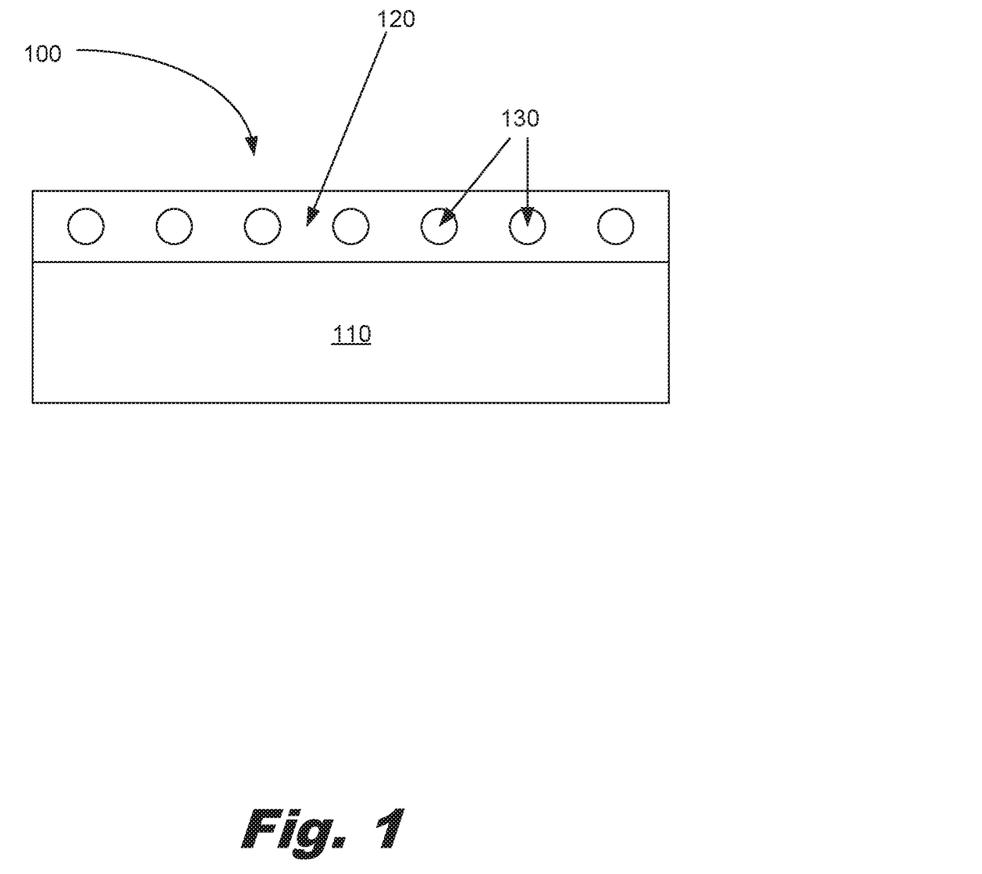
FIG. 1 is a cross-sectional diagram of a digital polymerase chain reaction (DPCR) test sample, according to one example of the principles described herein.

Turning now to the drawings, FIG. 1 is a cross-sectional diagram of a dPCR test sample, according to one example of the principles described herein. The test sample (100) comprises a substrate (110) with a layer of hydrophobic liquid (120) containing a primer suspended an aqueous droplet (130).

The test sample (100) may contain as few as a single aqueous droplet (130) suspended in the layer of hydrophobic liquid (120). In some examples, the test sample includes a relatively large number of aqueous droplets (130), for example, in excess of one thousand, four thousand, or ten thousand aqueous droplets. In one example, with a spacing of 150 droplets per inch, a square inch may contain 22,500 droplets. That corresponds to approximately 2.1 million droplets on an 8.5 inch by 11 inch sheet of material. At a spacing of 300 droplets per inch, the number of droplets rises to over 8 million. In one example, a sample (100) includes at least one thousand aqueous droplets (130) per square inch of substrate (110).

The substrate (110) may have a variety of forms and shapes. In one example, the substrate (110) is a sheet of hydrophobic polymer. Using a hydrophobic polymer may help stabilize the interaction between the hydrophobic liquid (120) and the substrate (110). Using a hydrophobic material as the substrate (110) also reduces the attraction between the aqueous droplet (130) and the substrate (110) which may help to keep the aqueous droplet (130) stable and suspended in the hydrophobic liquid (120).

The substrate (110) may be selected from a variety of materials. The substrate (110) may be polymer sheet or board. The substrate may be selected from pure forms and mixtures of polyethylene (PE), polypropylene (PP), polyethylene terephthalate (PET), polystyrene (PS), polycarbonate (PC), polyimide (PI), polyamide (e.g. Nylon), polyurethane (PU), polyether ether ketone (PEEK), polyester, epoxy, Poly(methyl methacrylate) (PMMA), polyvinylchloride (PVC), cellophane, Polyacetylene, Polyetherimide (PEI), and similar materials and substitutes. Non polymer materials may also be selected for the substrate (110), for example, metals or metalized films and glasses provide the ability to make optical measurements either by transmission or by a combination of transmission and reflection. These materials include surface oxides (either metal oxides or silicon-oxides) that are hydrophilic. Accordingly, in some examples, a layer of hydrophobic material is applied to a glass, metal, or ceramic substrate to aid the stability of the aqueous droplets (130) and discourage contact between the aqueous droplets (130) and the substrate (110). The layer of hydrophobic material may be a mechanically, thermally, or chemically attached layer. For example, the surface of a nonpolymer material may be chemically coated with silane or an adhesive. A polymer film may be interposed between the nonpolymer material and the hydrophobic liquid, with the polymer film attached with an adhesive, thermally, or mechanically to the nonpolymer material.

In one example, the substrate (110) is non-porous. The substrate (110) may be a composite with a porous component overlaid with hydrophobic liquid (120). Because many hydrophobic liquids (120) tend to have low surface energy, hydrophobic liquids (120) may migrate through a porous substrate (110). In one example, a porous substrate (110) includes a backing and/or coating that prevents migration of the hydrophobic liquid (120). A test sample (100) may also include a removable cover that contains the hydrophobic liquid (120) during shipping and handling prior to use. In one example, the hydrophobic liquid (120) may be confined to wells or selected features on the substrate (110) to minimize migration of the hydrophobic liquid.

In one example, the substrate (110) includes alignment features to facilitate deposition. The substrate (110) may include pins, knobs, ridges, divots, openings, hollows, holes, etc. to allow rapid and reliable placement relative to a target position for an ejector. The alignment features may be located on the back of the substrate (110) so as to interact with a platen of an ejector system (described below). The alignment features may be on the top or sides of the substrate (110). The alignment features may provide configuration information to an ejector system about the locations of the deposition regions on the substrate (110). In one example, the platen includes a plurality of holes corresponding with tapered, self-aligning cones on the substrate (110). In another example, the substrate may include the holes and the platen may have conic alignment pins to facilitate placement.

In one example, the layer of hydrophobic liquid (120) is mineral oil. For example, the hydrophobic liquid (120) may be IsoPar™ L produced by ExxonMobil® Chemical. In one example, the layer of hydrophobic liquid (120) is a layer of silicone oil. The hydrophobic liquid (120) may be a natural oil or a synthetic oil. In an example, the hydrophobic liquid (120) may be a mixture of materials.

The layer of hydrophobic liquid (120) is, in one example, approximately 1 millimeter thick. In some examples, the layer of hydrophobic liquid (120) is between 0.050 and 2.5 millimeters thick. In one example, the layer of hydrophobic liquid (120) is between 0.050 and 10 millimeters thick. Increasing the thickness of the layer of hydrophobic liquid (120) may increase the separation of the aqueous droplets (130) from the substrate (110). Increasing the thickness of the layer of hydrophobic liquid (120) also may increase the separation between the droplets (130) and a cover (description below). A relatively thicker layer of hydrophobic liquid (120) may provide additional protection and isolation for the aqueous droplets (130).

The aqueous droplet (130) may be formed from a single firing of a printhead, the printhead containing a solution with the same composition as the aqueous droplet (130). The aqueous droplet (130) may be formed by multiple firings from a single printhead containing a solution with the same composition as the aqueous droplet (130). The printhead may include a plurality of ejectors. For example, the printhead may include approximately 100 ejectors firing at approximately 10 kHz, Such a printhead could deposit approximately 1 million droplets per second. Even using multiple ejections to form a given aqueous droplet (130), this deposition rate facilitates rapid sample preparation. In one example, the printhead fires multiple solutions and mixes the solutions in the deposited aqueous droplets (130).

The aqueous droplets (130) in the hydrophobic liquid (120) layer may contain primers. A primer is a strand of short nucleic acid sequences (generally about 10 base pairs). Primer as used in this specification and the associated claims includes oligomers capable for supporting PCR-based amplification of a target. In one example, all the non-control aqueous droplets (130) in the hydrophobic liquid (120) layer contain copies of a primer.

The primers in the aqueous droplets (130) may be of a single type. The aqueous droplets (130) may include multiple types of primers in different aqueous droplets (130), for example, aqueous droplets (130) in a first portion of the test sample (100) may include a primer for a first allele while a second portion of the test sample (130) may include a different primer for a second allele for the same gene. Individual aqueous droplets (130) may include multiple types of primers, for example, individual aqueous droplets (130) may contain primers for multiple alleles for a given gene. The aqueous droplets (130) may contain a master mix. A master mix is a solution that includes the proteins and enzymes, such as polymerase, to run a PCR reaction. A given aqueous droplet (130) may contain a target piece of genetic material to be amplified, for example, DNA, RNA, cDNA, etc. In dPCR, some of the droplets will not contain copies of the target.

The aqueous droplet (130) may contain: water, primers; a polymerase enzyme; deoxynucleotide triphosphates (dNTPs); and a target sequence for replication. In one example, the polymerase is DNA polymerase. In another example, the polymerase is RNA polymerase. Some control droplets may contain: water, primers; a polymerase; and dNTPs. The aqueous droplets (130) may additionally contain surfactants, e.g., Tween 20. The aqueous droplets (130) may additionally contain ionic species, e.g. KCl. The aqueous droplets (130) may additionally contain a viscosity agent, e.g. polyethylene glycol.

The aqueous droplet (130) may be formed from multiple firings of multiple inkjets wherein the inkjets contain a plurality of solutions and the ejected droplets combine to form the aqueous droplet (130) with the desired composition. For example, one inkjet may deposit a master mix and form the initial aqueous droplet (130). A second inkjet may deposit a droplet with a target for amplification into the aqueous droplet (130). A third inkjet may deposit a droplet containing primers into the aqueous droplet (130). By selecting which inkjets contribute to the aqueous droplet (130) a variety of aqueous droplets (130) may be formed, including controls with no target for amplification, samples with variant primers for allele testing, etc.

The aqueous droplets (130) may be deposited in a pattern. For example, the aqueous droplets (130) may be deposited in a grid or hexagon pattern into the oil film. The spacing between droplets (130) in the X and Y direction may be the same or different among the droplets (130). In one example, samples were printed with 150 droplets per inch in an X direction and 150 droplets per inch in a Y direction. This droplet density can produce a total of 150×150 droplets per square inch or 22,500 droplets per square inch. Going to 300 droplets per square inch increases the number of samples to over 8 million on an 8.5"×11" substrate. This approach allows a large number of samples in a small area, for example at least 1,000 per square inch. Notably, traceability of the individual aqueous droplets (130) may be maintained due to the positional stability of the aqueous droplets (130) in the hydrophobic liquid (120) especially after a cover is in place.

In one example, the aqueous droplets (130) are deposited in a pattern that encodes information. For example, the aqueous droplets (130) may be deposited to spell out test information or sample identification. The pattern of aqueous droplets (130) may include registration marks to indicate sample identity. For example, omitting a droplet at the edge of a column of droplets may be used to indicate the start of a new sample configuration. A grid pattern may include spaces between clusters of droplets to indicate counts or alphanumeric information. For example, a series of nine droplets followed by an empty space followed by a series of twenty-two droplets followed by a second empty space may convey 9-22 or the pair of letters, e.g. i-u, using a simple alphabetical order based substitution code (A=1, B=2, etc.), a frequency code may achieve even higher information densities. More complex encoding mechanisms beyond simple counts may also be imagined and the present specification contemplates the use of these relatively more complex encoding mechanisms to include more information in the physical sample. For example, the sample conditions, batch numbers, compositions, date, time, and similar information may be encoded in the droplet pattern.

The aqueous droplets (130) may also include breaks in the array between sample sets. For example, a first primer configuration may be deposited in the first 10,000 samples. An empty line may be included to separate the sample sets and then a second primer configuration may be deposited in a second 10,000 samples. The first and second sets of aqueous droplets (130) may have different volumes per aqueous droplet (130) or other physical differences in addition to the compositional differences.

The pattern of the aqueous droplets (130) may also be used to provide information or identify samples. For example, a first sample set may be a traditional grid. A second sample set may be a hexagonal or triangular pattern. A third sample set may have a first separation in an X axis and a second separation in a Y axis. A fourth sample may have a jitter to the droplets in one axis to introduce non-linearity to the droplets. A fifth sample may include patterning information as discussed above. A sixth sample may include registration information introduced outside the intersections of the grid. In short, there are a wide range of methods for programming different sample configurations into a sheet of hydrophobic liquid (120) with aqueous droplets (130) suspended therein. Given 22,500 potential droplet positions in a square grid of 150 droplets per inch, a square inch may contain two sets of 10,000 samples plus a thousand characters of information which is certainly enough to provide robust sample identification. This ignores the additional increases in information density that could be achieved by encoding or similar methods.

Figure 2:
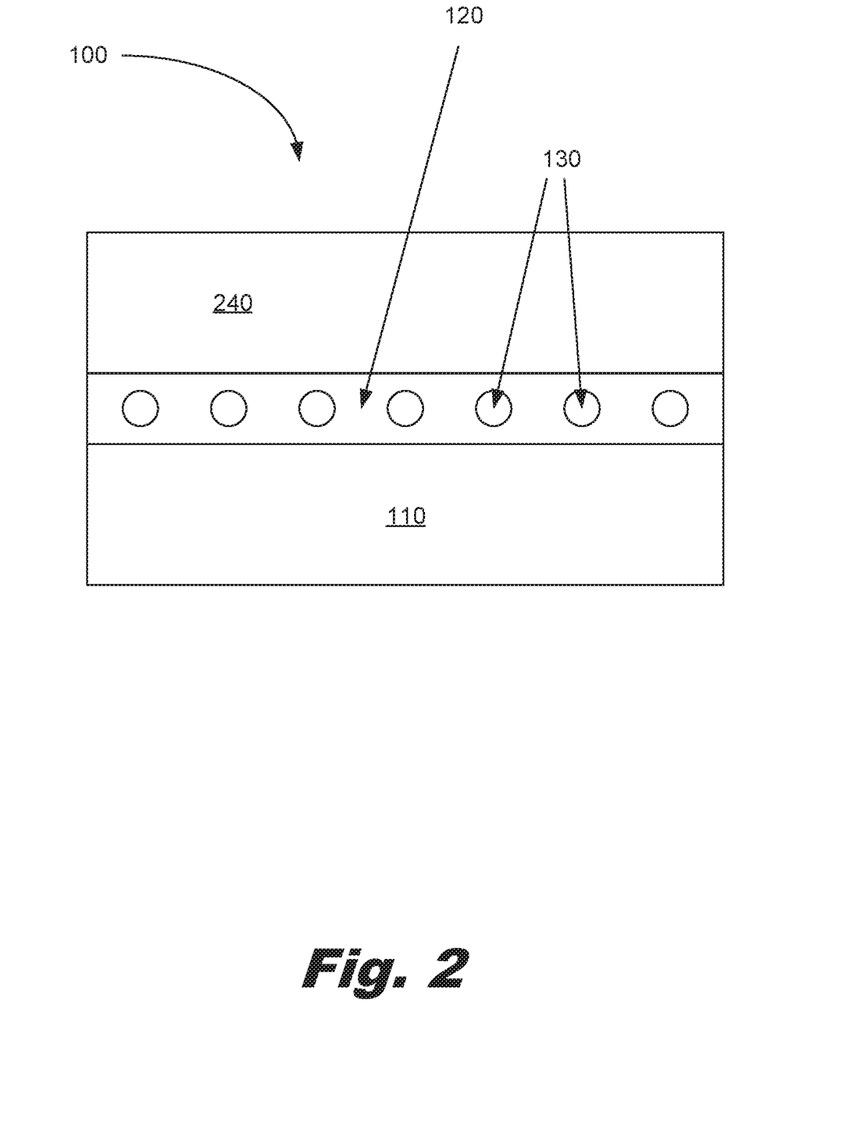
FIG. 2 is a cross-sectional diagram of a dPCR test sample, according to one example of the principles described herein.

FIG. 2 is a cross-sectional diagram of a dPCR test sample (100), according to one example of the principles described herein. The test sample (100) comprises a substrate (110) with a layer of hydrophobic liquid (120) containing a suspended an aqueous droplet (130). A cover (240) covers the top of the layer of hydrophobic fluid (120). The cover (240) serves to protect the test sample (100) from disruption.

The cover (240) is placed over the layer of hydrophobic liquid (120). In one example, the cover (240) includes a second layer of hydrophobic liquid on the side that contacts the first layer of hydrophobic liquid (120). In one example, the first and second layers of hydrophobic liquid are thin, for example, between 0.5 millimeters and 2 millimeters in thickness. During operation, when the cover (240) is placed over the substrate (110), the two layers contact and form a single layer of hydrophobic liquid (120).

The cover (240) may have a pressure sensitive adhesive on a portion of the bottom side. The pressure sensitive adhesive may seal the cover (240) to portions of the substrate (110) when the cover (240) is applied. The adhesive may be removable allowing the cover (240) to be peeled open, deposition of the aqueous droplets (130) to be performed, and then the cover (240) replaced.

In one example, the cover (240) is the same material as the substrate (110). The cover (240) may be a different material as the substrate (110). The cover (240) may be transparent. The cover (240) may include registration features or similar marks to aid in measuring the properties, positions, or alignment of the aqueous droplets (130).

The cover (240) may be a hydrophobic polymer. In one example, the cover (240) is a polymer film including, for example, polyethylene (PE, LDPE, HDPE) or polypropylene (PP). The cover may also be a more rigid polymer, for example, polystyrene (PS), polyethylene terephthalate (PET), polycarbonate (PC), polyimide (PI), etc. In one example, the cover (240) may be a glass or a coated glass. In one example, the cover (240) is reflective and the aqueous droplets (130) are assessed through the substrate (110) and off the reflection from the cover (240). The cover (240) may be a metalized polymer, a metal film, or a metal sheet. The cover (240) may be a composite. In another example, the substrate (110) may be reflective and the cover (240) transparent.

In one example, the substrate (110) has a cover (240) in place over the layer of hydrophobic liquid (120). During use of the test sample (100), the cover (240) is removed and the droplets formed in the hydrophobic liquid (130). The cover (240) is then replaced to protect the samples from contamination. The cover (240) may also reduce migration of the hydrophobic fluid (120).

The cover (240) may include a film underneath the cover contacting the hydrophobic liquid (130). The film may make exposing the hydrophobic liquid (130) easier to automate, for example, by including a tab and/or other feature to interact with an automated system. The cover (240) may include optical properties to facilitate measurement of the aqueous droplets (130). For example, the cover (240) may include a waveguide, a polarizing filter, a wavelength specific filter, a reflective surface, a selectively absorbing material, etc.

Figure 3:
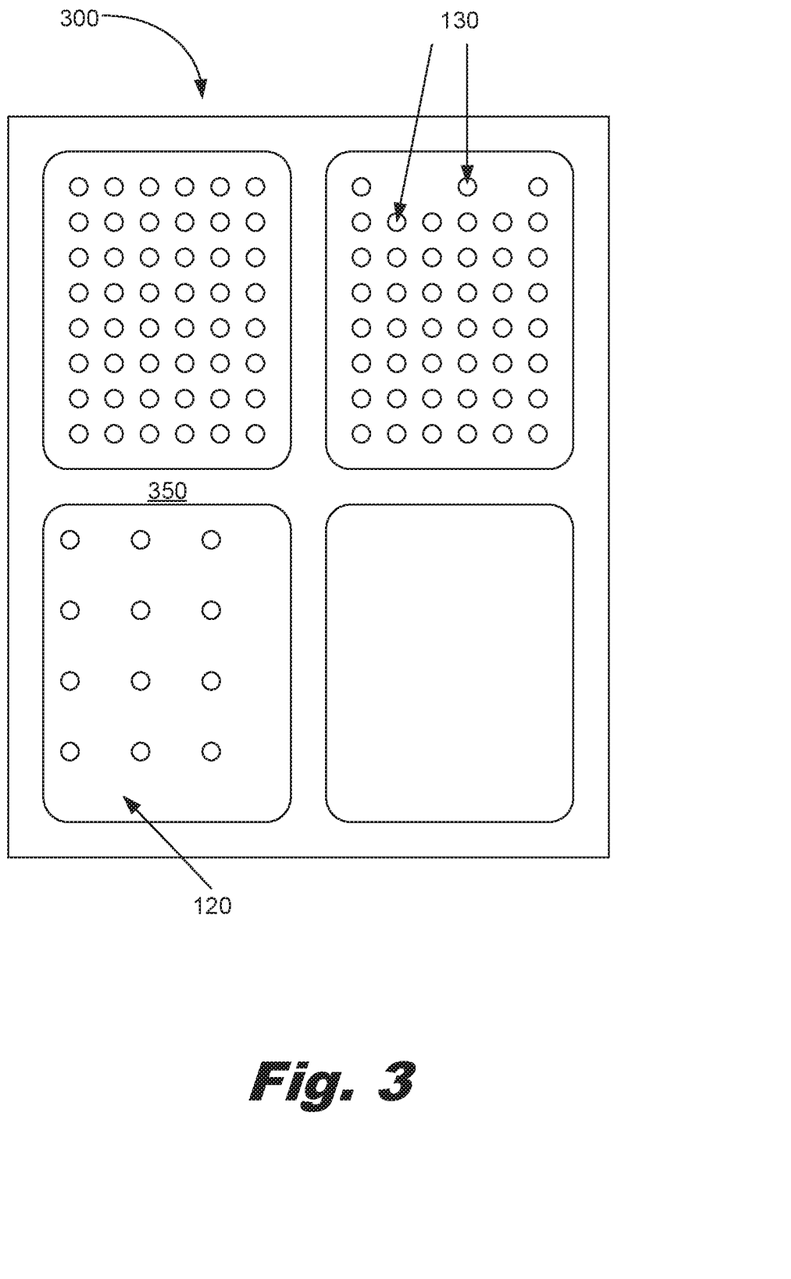
FIG. 3 is a top view of a dPCR test sample, according to one example of the principles described herein.

FIG. 3 is a top view of a dPCR test sample (300), according to one example of the principles described herein. In this example, the deposition areas which include a layer of hydrophobic liquid (120) have been divided into four areas. A divider (350) passing between the areas separates the areas and providing a contact point for a cover (240), Aqueous droplets (130) have been deposited in a variety of patterns in three of the four deposition areas.

The divider (350) may facilitate exposure or sealing of portions of the hydrophobic liquid (120) layer. The divider (350) may provide points for adhesive attachment of the cover (240) to the substrate (110). The divider (350) may include marking, orientation indicators, or other information to aid sample identification or preparation.

Figure 4:
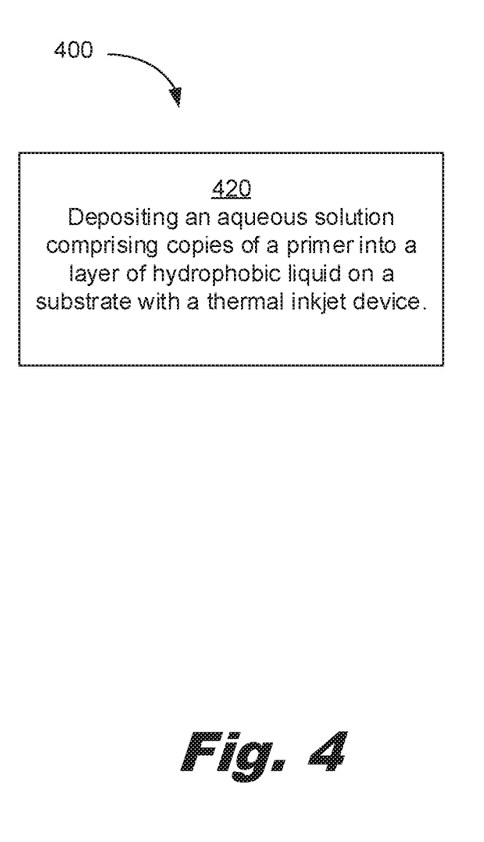
FIG. 4 is a flowchart showing a method of generating a dPCR test samples, according to one example of the principles described herein.

FIG. 4 is a flowchart showing a method (400) of generating dPCR samples, according to one example of the principles described herein. The method (400) includes depositing (block 420) an aqueous solution including copies of a primer into a layer of hydrophobic liquid on a substrate with a thermal inkjet device.

Thermal inkjets use a heating element, often a resistor, to rapidly heat and vaporize a liquid and form an expanding gas bubble. The bubble expands and expels a droplet from a nozzle. The bubble then collapses and new liquid is provided to the firing chamber to prepare for the next firing. Thermal inkjets are often part of a print head. The printhead may include multiple inkjets as well as fluid routing and signal lines to control and coordinate firing of the inkjets. Some print heads fire a single fluid from all the associated inkjets. Some printheads fire different fluids from different inkjets. For example, three color printing uses three color inks plus black ink is an example of a multiple fluid printhead.

Other operations that may be included in the method (400), in any combination, include: depositing the aqueous solution to form a pattern of water droplets within the hydrophobic liquid; wherein the water droplets are uniform in size; wherein the water droplets comprise a first group of droplets with a first uniform size and a second group of droplets with a second uniform size; wherein a water droplet within the hydrophobic liquid is formed from multiple firings by the thermal inkjet; wherein the hydrophobic liquid is a mineral oil; wherein the aqueous solution further comprises a master mix and a deoxyribonucleic acid (DNA) fragment; wherein the aqueous solution further comprises a master mix and a ribonucleic acid (RNA) fragment; performing a polymerase chain reaction (PCR) to amplify a target in a droplet of the aqueous solution; applying a cover over the layer of hydrophobic liquid; measuring a property of the droplets in the pattern of droplets; wherein measuring a property of the droplets in the pattern of droplets is performed simultaneously on a plurality of droplets.

Figure 5:
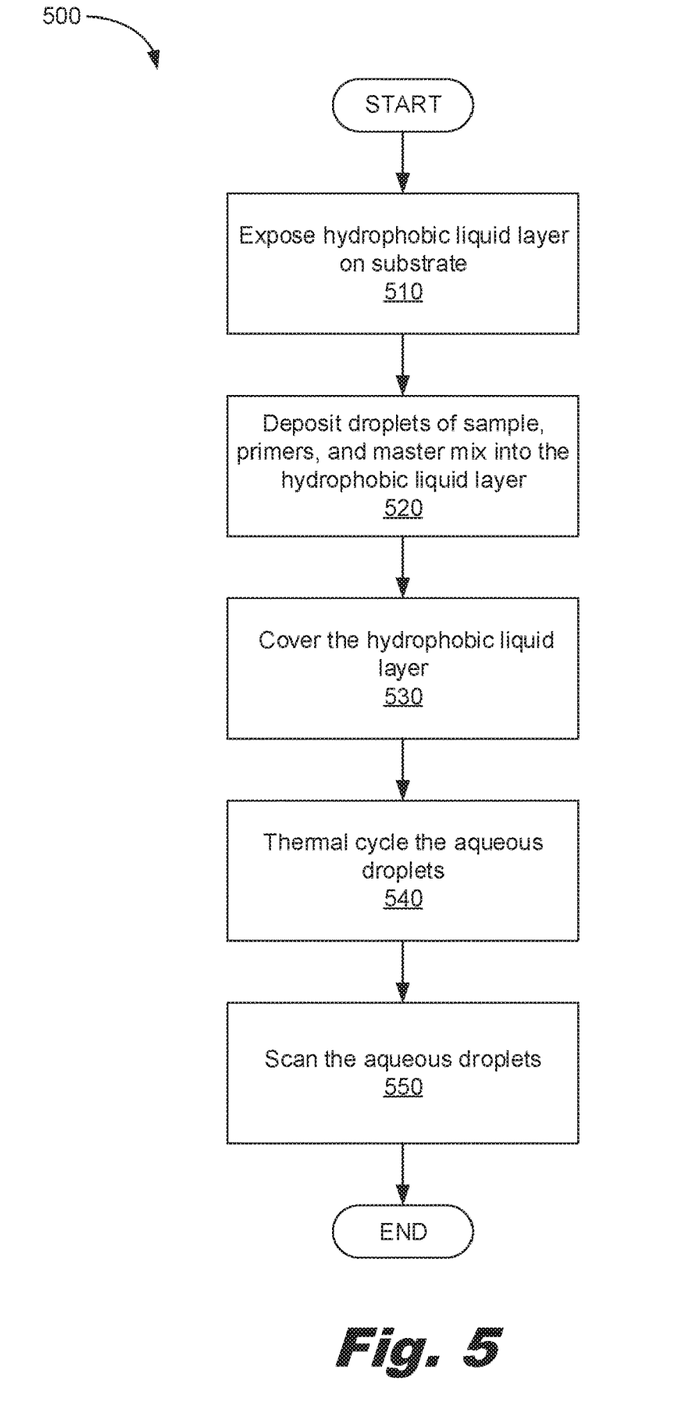
FIG. 5 is a flowchart showing a method of performing dPCR testing, according to one example of the principles described herein.

FIG. 5 is a flowchart showing a method of performing dPCR testing, according to one example of the principles described herein. The method (500) comprises: expose (510) a hydrophobic liquid layer (120) on a substrate (110); deposit (520) aqueous droplets of sample, primers, and master mix into the layer of hydrophobic liquid (120); cover (530) the hydrophobic liquid (120) layer; thermal cycle (540) the aqueous droplets (130); and scan (550) the aqueous droplets (130). While FIG. 5 shows each of these operations as distinct, the operations may be combined or executed in any suitable order. For example, the scan (550) operation may be conducted simultaneously with the thermal cycle (540) such that thermal cycling continues until a set of control droplets are reliably detected or some similar end condition. In one example, a control aqueous droplet (130) in the hydrophobic liquid layer (120) contains an indicator for double stranded genetic material or for a specific sequence of single stranded genetic material. The thermal cycle (540) operation is conducted until the signal from this control aqueous droplet (130) reaches a given threshold indicating a sufficient number of replications to allow reliable determination of the presence or absence of a target sequence in other aqueous droplets (130). Similarly, portions of the hydrophobic liquid (120) layer on the substrate may be selectively exposed and covered as part of the deposition process to minimize the time the hydrophobic layer (120) is uncovered and exposed to potential contaminants.

Expose a hydrophobic liquid layer (120) on a substrate (110). In one example, the substrate (110) or a removable layer over the hydrophobic liquid (120) includes an adhesive that hold the removable layer in place during transportation and after placement of the cover (240). In one example, the removable layer is a transparent polymer film, e.g. PET. Such a film may accommodate marking, for example with overhead projector or dry erase markers to provide visual identification of the associated samples. The scan (550) may include detection of such writing and compensation for the writing in the sample assessment. The scan (550) may also provide an OCR capability and attach such writing to the output file as an image or text to facilitate sample traceability.

In another example, expose a hydrophobic liquid layer (120) on a substrate (110), may be replaced by forming the hydrophobic liquid layer (120) on the substrate (110). For example, this may be as simple as applying a quantity of hydrophobic liquid (120) to a selected portion of the substrate (110). Many hydrophobic liquids (120), for example, mineral oils, will self-level in a reasonable time frame. However, allowing the liquid to reach a reasonably stable condition may help keep the alignment of the aqueous droplets (130) deposit in the hydrophobic liquid (130) orderly after deposition.

Deposit (520) droplets of sample, primers, and master mix into the hydrophobic liquid layer may be performed using a thermal inkjet (TIJ) or piezoelectric inkjet (PIJ) printhead. In one example, the sample, primer, and master mix are mixed into a common solution that is provided to the printhead. In a second example, a component is provided separately and mixed in the printhead. In a third example, a component is provided separately and deposited separately into the aqueous droplets (130) in the hydrophobic fluid (120). In a fourth example, multiple types of one of the components are provided to the printhead, e.g., two different types of primers could be supplied separately to identify an allele, Mixing may be performed in the printhead or by depositing multiple ejections into a common droplet in the hydrophobic liquid (120).

In one example, the printhead comes preloaded with primers and master mix and accommodates a sample from a user. The user sample is then deposited over a pattern of aqueous droplets of the primers and master mix to form multiple test samples in a common hydrophobic liquid (120) layer on a substrate (110). For example, the printhead may include primers to detect all or some alleles of a gene or group of related genes, allowing a single sample to be used to assess the various alleles of the genes to be tested. In one example, the printhead is provided as a disposable as part of a kit including a test sample (100) for conducting the test. In similar example, the printhead may include a number of sample provision ports associated with different ejectors to avoid cross-contamination.

Cover (530) the hydrophobic liquid (120) may be replacing a shipping cover (240) over the hydrophobic liquid (120). Cover (530) the hydrophobic liquid (120) may be applying a new cover (240). The cover (240) may include a layer of hydrophobic liquid (120) to contact the hydrophobic liquid (120) on the substrate (110) in order to maintain good separation between the cover (240) and the aqueous droplets (130). In some examples, cover (530) the hydrophobic liquid may include securing the cover (240) to the substrate (110) using adhesive. The adhesive may be a pressure sensitive adhesive. The adhesive may be applied to the substrate (110) after deposition of the aqueous droplets (130). The adhesive may include a backing that is removed prior to covering the hydrophobic liquid (120).

Thermal cycle (540) the aqueous droplets may be performed using an oven or a bath. In one example, the sample is placed on a thermal sink and a heating apparatus is rastered across the sample. This allows the thermal source to be kept at a constant temperature while providing thermal cycling to the aqueous droplets (130) in the hydrophobic liquid (120). The heating apparatus may be an IR source, a heater, and/or a microwave source. In one example, the rastering apparatus also includes a scan head that accumulates scan data during the thermal cycling.

The equipment performing the thermal cycling may include a non-contact thermal probe to monitor and control the cycling time. In a second example, the thermal probe is used to detect deviations from the desired thermal cycling profile. The thermal probe may be attached to the rastering apparatus. The thermal probe may target aqueous droplets (130) being heated. The thermal probe may target aqueous droplets (130) being cooled. The thermal probe may sample a larger area of the substrate (110), the measured larger area including a plurality of aqueous droplets (130).

Scan (550) the aqueous droplets (130) to detect the presence or absence of an amplified target. The scan (550) may include individualized scan of individual droplets, for example, using a laser or similar focused source. In one example, this is performed in a one-up manner. The scan (550) may be detection using a flood illumination and a sensor array located to detect changes in signal from the flood illumination. In one example, the scan (550) includes capturing a photograph, either traditional film or a digital image. In some examples, absorbing or emitting components are added to the aqueous droplets (130) such that aqueous droplets with DNA samples longer than a primer provide a detectable output when illuminated or otherwise activated, for example by thermal activation.

The ability to capture the whole data sample as a single image allows the data processing to be provided as part of the existing equipment or by a secondary resource, for example, a remote server. In one example, a processor converts an image into a series of binary determinations about individual aqueous droplets and stores that information in an associated file or the same file. Any data encoded in the droplet patterns mays similarly be extracted and stored. Any information written on the sample may be extracted and stored, including serial or model information on the substrate. In one example, the stored information also includes processing information provided by equipment used to thermal cycle the samples, for example, number of cycles, temperature range, etc.

Figure 6:
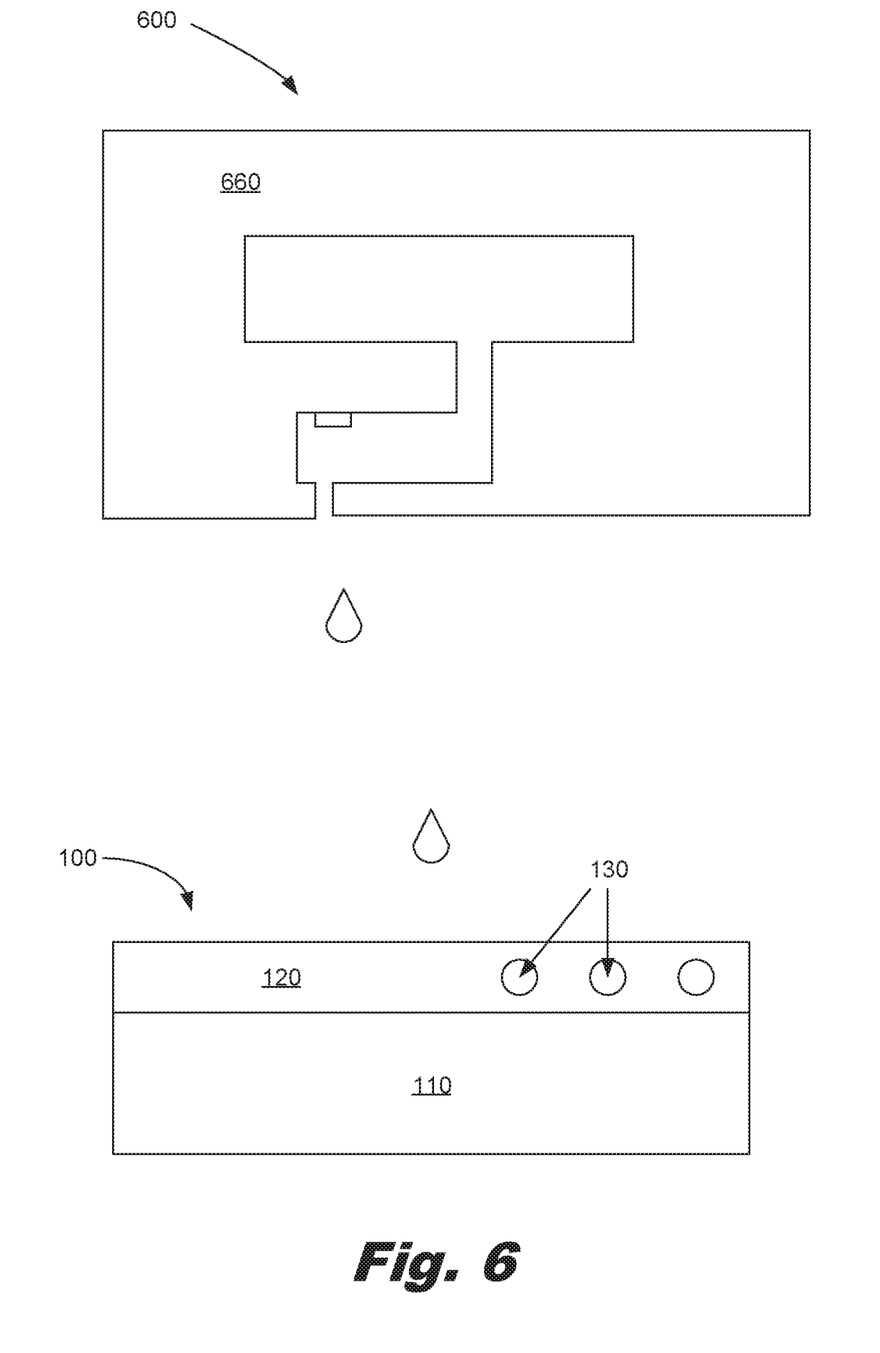
FIG. 6 is a cross-sectional diagram of system for generating dPCR samples, according to one example of the principles described herein.

FIG. 6 is a cross-sectional diagram of system (600) for generating dPCR samples, according to one example of the principles described herein. The system (600) comprises: a printhead (660), the printhead (660) containing an aqueous fluid including: water, primers, master mix, and a target sequence to be amplified; and a substrate (100) positioned to receive droplets ejected from the printhead (660), the sample (100) including: a substrate (110) and layer of hydrophobic liquid (120) on the substrate; wherein droplets ejected by the printhead (660) are embedded in the layer of hydrophobic liquid (120).

The printhead (660) may be a thermal inkjet (TIJ) or piezoelectric inkjet (PIJ). The printhead (660) may contain just a single fluid mixture for ejection. The printhead (660) may include a plurality of fluids for ejection. The printhead (660) may form deposited droplets of aqueous solution (130) in a hydrophobic liquid (120) using multiple ejections per droplet. The printhead (660) may form each deposited aqueous droplet (130) in the hydrophobic liquid (120) layer with a single ejection.

The printhead (660) may mix solutions internally. The printhead (660) may include fluid handling or microfluidic components to facilitate solution preparation prior to ejection. The printhead (660) may include a number of inlet ports to receive fluid for ejection. The printhead (660) may come preloaded with a solution or with multiple solutions. The printhead (660) may include a standardized port.

Within the principles described by this specification, a vast number of variations exist. The examples described are examples, and are not intended to limit the scope, applicability, or construction of the claims.

What is claimed is:

1. A method of preparing a sample, the method comprising:
    removing a cover from a substrate to expose a first layer of hydrophobic liquid on the substrate, wherein the cover comprises a second layer of the hydrophobic liquid;
    depositing, with a thermal inkjet printhead, droplets of an aqueous solution comprising copies of a primer into the first layer of hydrophobic liquid on the substrate; and
    replacing the cover over the substrate to form a single layer of the hydrophobic liquid as the first layer and the second layer contact one another and suspending the droplets in the single layer.

2. The method of claim 1, further comprising:
    depositing the aqueous solution to form a pattern of droplets of aqueous solution within the first layer of hydrophobic liquid.

3. The method of claim 2, wherein the droplets of aqueous solution are uniform in size.

4. The method of claim 2, wherein the droplets of aqueous solution comprise a first group of droplets with a first uniform size and a second group of droplets with a second uniform size.

5. The method of claim 2, wherein a droplet of aqueous solution within the first layer of hydrophobic liquid is formed using multiple firings by the thermal inkjet printhead.

6. The method of claim 2, further comprising measuring a property of the droplets in the pattern of droplets.

7. The method of claim 6, wherein measuring a property of the droplets in the pattern of droplets is performed simultaneously on a plurality of droplets.

8. The method of claim 1, wherein the hydrophobic liquid is a mineral oil.

9. The method of claim 1, wherein the aqueous solution further comprises a master mix and a deoxyribonucleic acid (DNA) fragment.

10. The method of claim 1, wherein the aqueous solution further comprises a master mix and a ribonucleic acid (RNA) fragment.

11. The method of claim 1, further comprising performing a polymerase chain reaction (PCR) to amplify a target in a droplet of the aqueous solution.

12. The method of claim 1, wherein the substrate comprises dividers to separate areas for droplet deposition and to provide a contact point for the cover.

13. The method of claim 1, wherein:
    the cover is a thermally conductive cover; and
    the substrate is a thermally conductive substrate.

14. The method of claim 1, further comprising aligning, with alignment features on the substrate and a platen of an ejection system comprising the thermal inkjet printhead, ejectors of the thermal inkjet printhead to a location on the substrate.

15. The method of claim 1, wherein depositing an aqueous droplet comprises dispensing multiple droplets at a single location, each droplet being of a different compound to execute polymerase chain reaction.

16. The method of claim 1, further comprising encoding information in the sample by forming droplets in a pattern.

17. The method of claim 1, further comprising encoding an identification of the sample by forming droplets in a pattern of alphanumeric characters.

* * * * *